(12) United States Patent
DeNure

(10) Patent No.: US 6,307,672 B1
(45) Date of Patent: *Oct. 23, 2001

(54) MICROSCOPE COLLISION PROTECTION APPARATUS

(75) Inventor: Charles R. DeNure, Pocatello, ID (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/775,684

(22) Filed: Dec. 31, 1996

(51) Int. Cl.⁷ .............................. G02B 21/00; G02B 21/26
(52) U.S. Cl. .......................... 359/382; 359/383; 359/392
(58) Field of Search .................................. 359/382, 383, 359/391, 392, 819, 822

(56) References Cited

U.S. PATENT DOCUMENTS 5,453,881 * 9/1995 Suzuki ................................. 359/824

FOREIGN PATENT DOCUMENTS

0172612 * 9/1984 (JP) ...................................... 359/391
0121410 * 6/1985 (JP) ...................................... 359/392

* cited by examiner

Primary Examiner—Paul M. Dzierzynski
Assistant Examiner—Mark Robinson
(74) Attorney, Agent, or Firm—Colette C. Muenzen; William R. Moser; Paul A. Gottlieb

(57) ABSTRACT

A microscope collision protection apparatus for a remote control microscope which protects the optical and associated components from damage in the event of an uncontrolled collision with a specimen, regardless of the specimen size or shape. In a preferred embodiment, the apparatus includes a counterbalanced slide for mounting the microscope's optical components. This slide replaces the rigid mounts on conventional upright microscopes with a precision ball bearing slide. As the specimen contacts an optical component, the contacting force will move the slide and the optical components mounted thereon. This movement will protect the optical and associated components from damage as the movement causes a limit switch to be actuated, thereby stopping all motors responsible for the collision.

13 Claims, 3 Drawing Sheets

MICROSCOPE COLLISION PROTECTION APPARATUS

RIGHTS OF THE GOVERNMENT

The invention described herein was made or conceived in the course of or under a contract between the United States Department of Energy and the Westinghouse Electric Corporation, according to which the United States Government has rights in this invention and title thereto is in the Department of Energy.

FIELD OF THE INVENTION

The invention relates to remotely controlled microscopes and more particularly to prevention of damage of remotely controlled microscopes due to collision of the specimen and the lens while focusing.

BACKGROUND OF THE INVENTION

High magnification microscopes are often damaged when a specimen collides into the objective lens while the operator is focusing. Many high magnification lenses are designed to accommodate this by using lenses which non-destructively collapse under light pressure. Typically, the microscope operator will notice the collision and stop the focusing attempt.

A problem arises when a microscope is used in a remote location where the operator is some distance away, as is typically done in nuclear research. The operator has no feel and no direct visual contact with the microscope. Consequently, the operator does not know to stop the focus drive before severe damage occurs.

Over-travel control switches mounted on the stage are not useful if specimen sizes change. A limit switch position for small specimens will not suffice for large specimens. Infrared positioning is also not useful because the high radiation typically encountered in nuclear research will quickly damage the infrared system.

In light of these considerations, a need arises for a remote-control microscope which is protected from collision damage regardless of specimen size or shape.

SUMMARY OF THE INVENTION

The present invention is a microscope collision protection device for a remote control microscope which protects the objective lenses and all associated components from damage in the event of an uncontrolled specimen collision, regardless of the specimen size or shape. In a preferred embodiment, the device comprises a counterbalanced slide used for mounting the microscope's optical components. It replaces the rigid mounts found on all upright microscopes with a precision ball bearing slide.

As the specimen contacts the lens, the contacting force moves the optical package along the slide. This movement protects the objective lenses and all associated components from damage and will trip a limit switch, thereby stopping all motors responsible for the collision. The collision forces are minimized by the use of a counterweight. Owing to the use of this counterweight, the optical package weight is nearly balanced during normal operation, however, this optical package will move easily when contacted by the specimen while focusing.

DETAILED DESCRIPTION OF THE INVENTION

Figure 1:
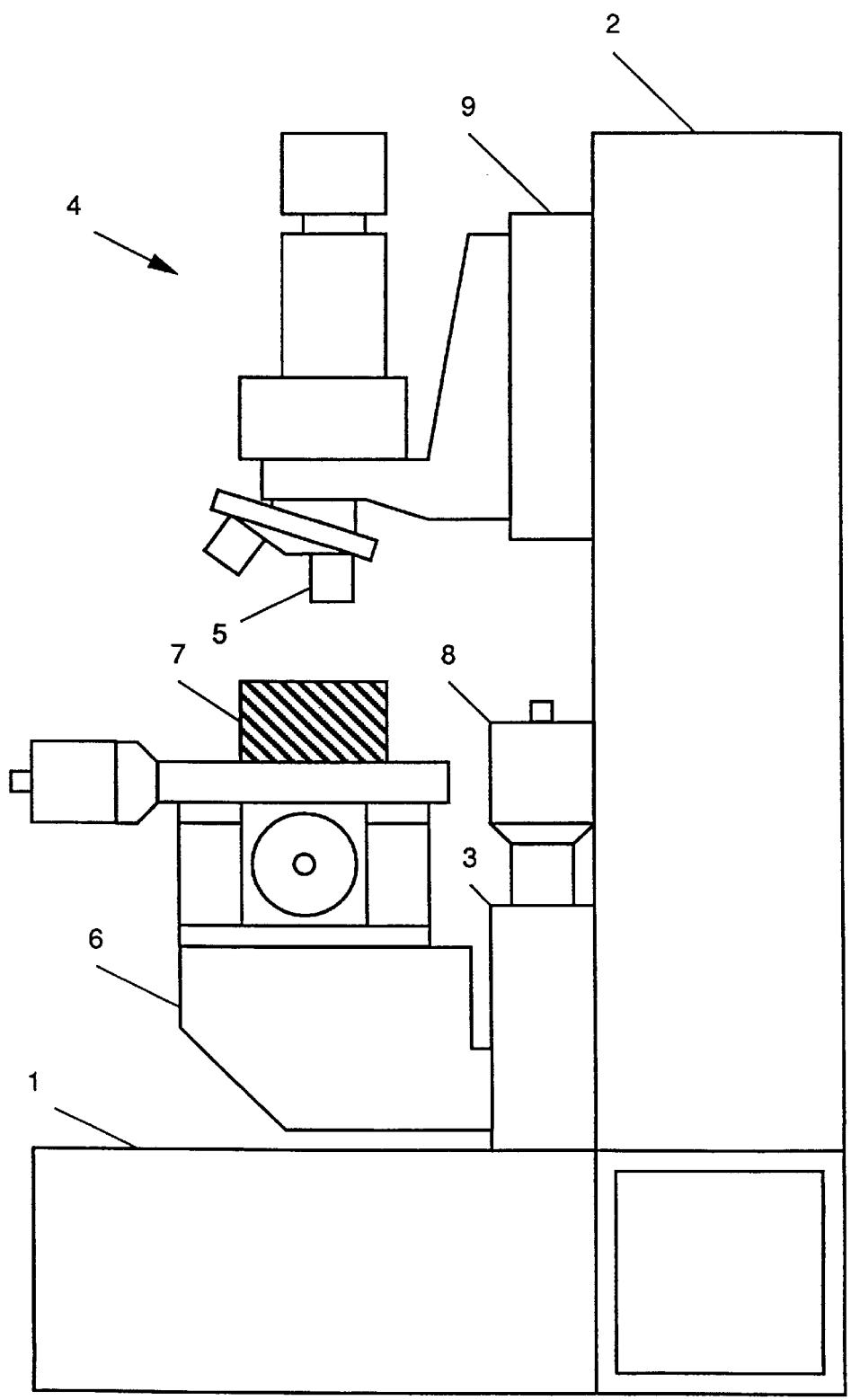
FIG. 1 is a view of a prior art, unprotected, remote control microscope.

FIG. 1 shows a prior art, unprotected microscope. The microscope includes a base 1, a vertical support member 2 projecting from base 1 and a stage support member 3 projecting from base 1. An optical package 4, including an objective lens 5, is attached to vertical support member 2 by mounting 9. Optical package 4 may include several lenses and a television camera or other sensors, but always includes at least one objective lens. Stage 6 is movably mounted on vertical support member 3 and supports specimen 7. Stage 6 is driven vertically by focusing drive motor 8, coupled by well-known means, such as, for example, a worm gear mechanism enclosed by stage support member 3. Motor 8 is controlled by an external controller (not shown), typically located at least several feet from the microscope.

Figure 2:
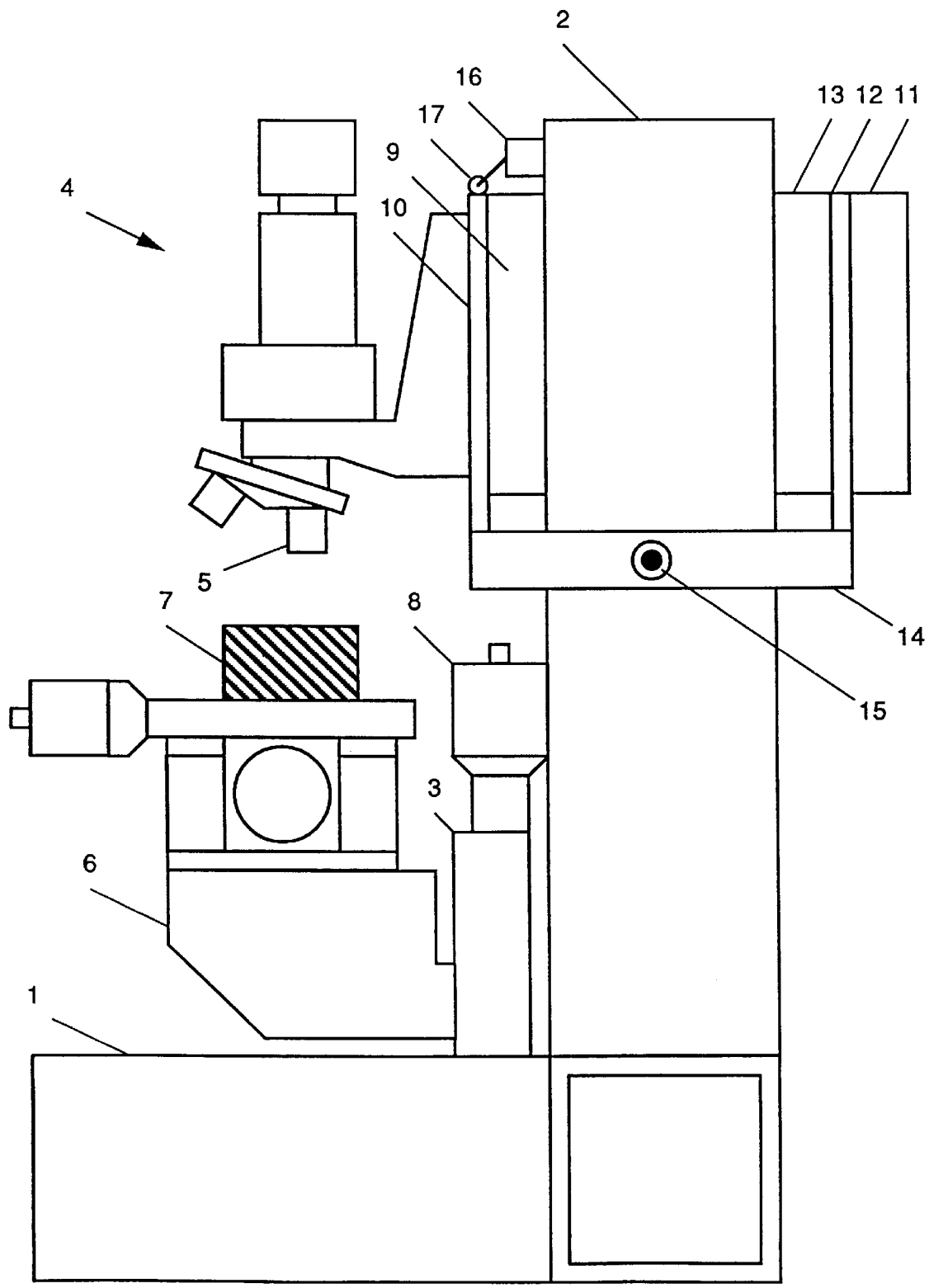
FIG. 2 is a view of a microscope incorporating a preferred embodiment of the present invention.

FIG. 2 shows a remote control microscope incorporating a preferred embodiment of the present invention. Optical package 4 is attached to slide 10. Slide 10 is attached to vertical support member 2 by mounting 9. A counterweight 11 is attached to slide 12, which is in turn attached to the opposite side of vertical support member 2 by mounting 13. Rocker arm 14 is pivotably mounted to vertical support member 2 by pivot 15. One end of rocker arm 14 is in contact with the movable portion of slide 10; the other end of rocker arm 14 is in contact with the movable portion of slide 12. Slides 10 and 12 are similar and are typically of ball bearing construction.

In normal operation, the force exerted by counterweight 11 on rocker arm 14 nearly balances the force exerted by optical package 4. There is a small net force exerted by optical package 4 which holds package 4 against a hard stop. This hard stop locates optical package 4 and provides vibration resistance. The hard stop may be provided by the travel limit of slide 10 or slide 12 or by a device such as a pin, bar or flange.

Limit switch 16 is attached to vertical support member 2 and is arranged so that in normal operation, actuator 17 is in contact with the movable portion of slide 10 and limit switch 16 is in the unactuated position. The unactuated position may be either normally open or normally closed depending on the requirements of the external controller. In applications not involving high radiation levels, limit switch 16 may be replaced by an optical sensor.

In one embodiment, counterweight 11 is replaceable with counterweights of various sizes. This allows optical packages of any reasonable size and weight to be accommodated with just simple changes in the counterweight.

Figure 3:
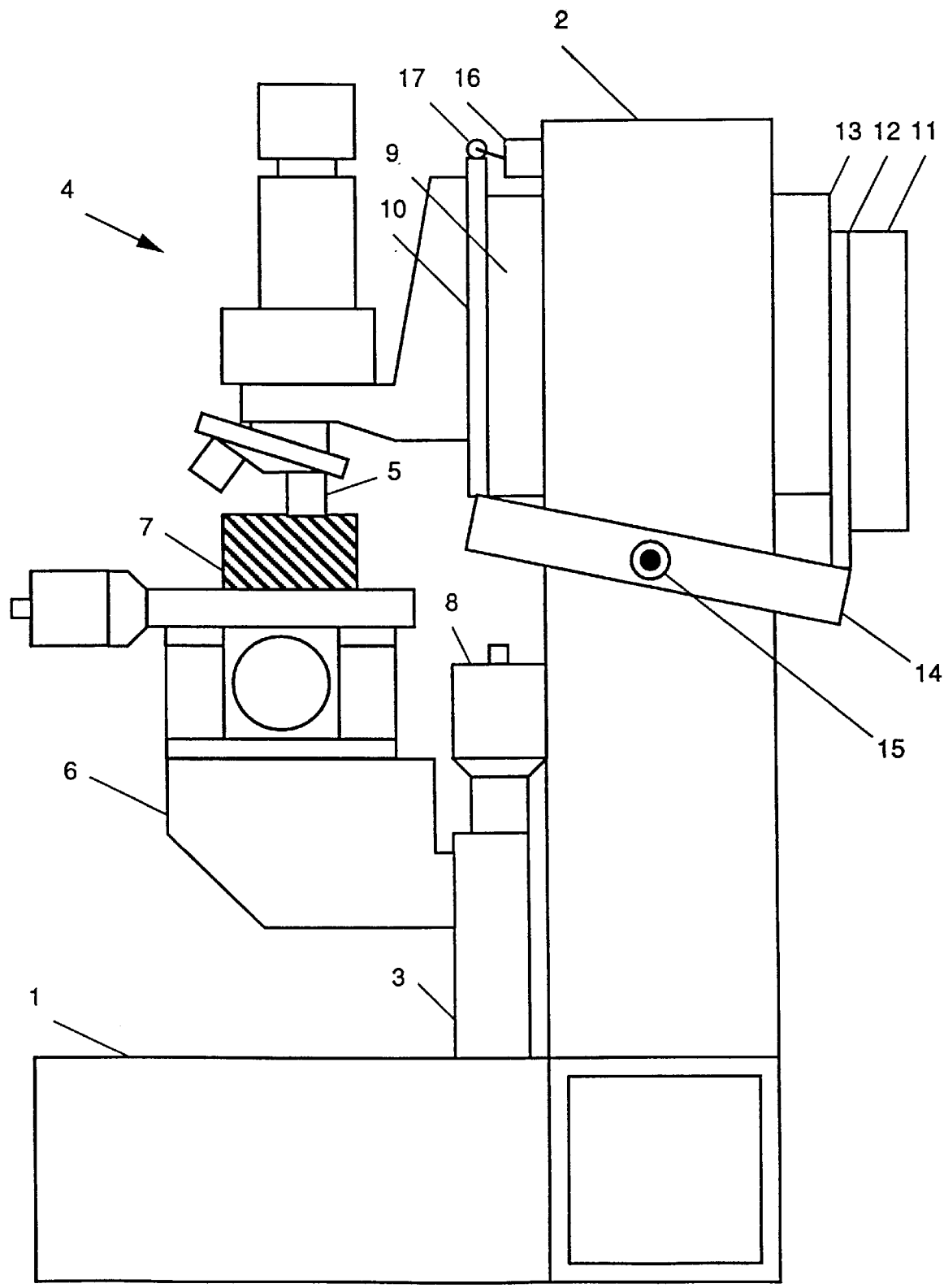
FIG. 3 is a view of a microscope incorporating a preferred embodiment of the present invention and showing the operation of the present invention in a specimen collision.

FIG. 3 shows a microscope incorporating a preferred embodiment of the present invention in which a collision has occurred between specimen 7 and objective lens 5. Motor 8 has driven stage 6 upwards until specimen 7 has come into contact with objective lens 5. When specimen 7 contacts lens 5, the contacting force moves optical package 4 upwards along slide 10. This movement protects the microscope from damage. The same protective movement may occur upon contact between the optical package 4 and the upper surface of stage 6 if the specimen 7 is absent.

As the movable portion of slide 10 moves upward, it moves actuator 17 of limit switch 16, actuating limit switch 16. When limit switch 16 is actuated, motor 8 is stopped, thereby preventing any damage to the objective lenses and all associated components. Typically, limit switch 16 is connected to the external controller which senses actuation of switch 16 and stops motor 8. Limit switch 16 is arranged so that it is actuated well before slide 10 reaches the limit of its travel and while rocker arm 14 is still in communication with slide 10. This ensures that the microscope and the specimen will not be damaged.

Although specific embodiments have been disclosed, it will be readily understood by persons skilled in the art that other, equivalent embodiments are possible, such as on microscopes with architectures that vary from the design described and shown herein. For example, the present invention is also effective on a microscope that raises and lowers the optical package 4 instead of the stage 6 to achieve a proper focus on the specimen. In one such alternative embodiment, the support member 3 and the motor 8 are mounted on the slide 10 and, instead of adjustably supporting the stage 6, the support member 3 adjustably supports the optical package 4. In this embodiment, the stage 6 may be vertically fixed to the base 1. The limit switch 16 and the actuator 17 would operate in the same manner as already described for the embodiment of FIG. 3.

As another alternative embodiment, the position of the support member 3 and motor 8 may be exchanged with the position of the slide mechanism components 10–15, such that the optical package 4 is vertically adjustable and the stage 6 moves only when there is contact between the optical package 4 and the specimen 7, or between the optical package 4 and the upper surface of stage 6 if the specimen 7 is absent. In this embodiment, the support member 3 and the motor 8 would be positioned in the place of mounting 9 and slide 10, and the mounting 9 and the slide 10 would be positioned in the place of support member 3 and motor 8. Accordingly, the stage 6 and the specimen 7 mounted thereon would be carried by the slide 10, and the remaining slide mechanism components 11–15 would be positioned at a correspondingly lower level such that the rocker arm 14 would tilt in the direction opposite to that shown in FIG. 3 upon contact between the optical package 4 and the specimen 7, or between the optical package 4 and the upper surface of stage 6 if the specimen 7 is absent. The limit switch 16 and its actuator 17 would be relocated to the rear side of the vertical support member 2 and placed in a correspondingly lower position so as to be actuated by upward movement of the slide 12 in response to downward movement of the slide 10.

What is claimed is:

1. An apparatus for protecting an optical package of a microscope from collision damage during focusing of the optical package on a specimen, said apparatus comprising:
    a first support member for supporting the specimen;
    a second support member for supporting the optical package;
    means for moving one of said support members relative to the other of said support members to focus the optical package on the specimen; and,
    means for slidably mounting the other of said support members on a base so that said other support member slides relative to said base to prevent damage to the optical package when the specimen supported by said first support member comes into contact with the optical package supported by said second support member.

2. The apparatus of claim 1, wherein said second support member is slidably mounted on said base so that said optical package slides relative to said base when the specimen supported by said first support member comes into contact with the optical package.

3. The apparatus of claim 2, wherein said moving means is mounted on said base for adjustment of said first support member relative to said second support member to focus the optical package on the specimen.

4. The apparatus of claim 3, wherein said mounting means comprises a counterweight arranged to counterbalance the weight of the optical package.

5. The apparatus of claim 4, wherein said mounting means comprises a first sliding member for carrying said optical package, a second sliding member for carrying said counterweight, and means for connecting said first and second sliding members so that movement of said first sliding member causes a corresponding counterbalancing movement of the second sliding member.

6. The apparatus of claim 5, wherein said connecting means comprises a rocker arm pivotably mounted on a vertical support member connected to said base.

7. The apparatus of claim 1 further comprising a limit switch for detecting that said other support member has moved relative to said base.

8. The apparatus of claim 7, wherein said moving means comprises a motor for causing said one support member to move relative to said other support member, and wherein said motor is stopped when said limit switch detects sliding movement of said other support member.

9. An apparatus for protecting an optical package of a microscope from collision damage during focusing of said optical package on a specimen, said microscope including a base, a motor-driven stage mounted on the base for holding the specimen, a vertical support member for supporting the optical package on the base to allow focusing of the optical package on the specimen, said apparatus comprising:
    a first slider slidably mounting the optical package on a first side of the vertical support member;
    a second slider slidably mounting a counterweight on a second side of the vertical support member; and,
    a rocker arm pivotably mounted on the vertical support member and connecting the first and second sliders to counterbalance the optical package with the counterweight, such that the optical package moves without being damaged when the specimen being held by said stage comes into contact with the optical package supported by said vertical support member.

10. The apparatus of claim 9 further comprising a limit switch positioned to be actuated in response to sliding movement of the optical package.

11. The apparatus of claim 10 further comprising means for stopping the motion of the motor-driven stage when the limit switch detects sliding movement of the optical package.

12. The apparatus of claim 9, wherein the counterweight is removably mounted on said second slider.

13. An apparatus for protecting an optical package of a microscope from collision damage during focusing of said optical package on a specimen, said microscope including a base, a motor-driven stage for holding the specimen and mounted for motion relative to the base, a vertical support member for supporting the optical package on the base to allow focusing of the optical package on the specimen, said apparatus comprising:

a first slider slidably mounting the optical package on a first side of the vertical support member;

a second slider slidably mounting a removable counterweight on a second side of the vertical support member;

a rocker arm pivotably mounted on the vertical support member and connecting the first and second sliders to counterbalance the optical package with the counterweight;

a limit switch positioned to be actuated in response to sliding movement of the optical package; and, means for stopping the motion of the motor-driven stage in response to actuation of the limit switch, such that the optical package moves without being damaged when the specimen being held by said stage comes into contact with the optical package, wherein motion of the motor-driven stage is stopped when the limit switch detects that the optical package has moved.

* * * * *